(12) United States Patent
Swayne et al.

(10) Patent No.: US 10,006,817 B2
(45) Date of Patent: Jun. 26, 2018

(54) ADJUSTABLE-LENGTH TEMPERATURE PROBE

(71) Applicant: Electrolux Home Products, Inc., Charlotte, NC (US)

(72) Inventors: Steven M. Swayne, Hendersonville, TN (US); Brendan McGinnis, Russellville, KY (US); Elizabeth A. Byrne, Orlinda, TN (US)

(73) Assignee: Electrolux Home Products, Inc., Charlotte, NC (US)

( * ) Notice: Subject to any disclaimer, the term of this patent is extended or adjusted under 35 U.S.C. 154(b) by 376 days.

(21) Appl. No.: 14/714,745

(22) Filed: May 18, 2015

(65) Prior Publication Data

US 2016/0341607 A1 Nov. 24, 2016

(51) Int. Cl.
*G01K 7/00* (2006.01)
*G01K 13/00* (2006.01)
(Continued)

(52) U.S. Cl.
CPC ............... *G01K 13/00* (2013.01); *G01K 1/02* (2013.01); *G01K 7/00* (2013.01); *G01N 33/12* (2013.01);
(Continued)

(58) Field of Classification Search
CPC .... H05B 1/0263; H05B 6/6452; G01N 33/12; G01N 25/72; G01N 33/02; G01K 7/00; G01K 1/02; G01K 13/00; G01K 7/02; G01K 3/005; G01K 3/10; G01K 7/42; G01K 7/22; G01K 13/02; G01K 2205/04; G01K 7/10; G01K 11/32; G01K 2013/024; H01R 4/023; H01R 4/029; H01R 43/28; B23K 31/02; G01F 1/00; H05K 7/20945; F24F 11/0012; F24F 2001/0052; F24F 2011/0093; F24F 11/022; H02M 1/32; H02M 1/38; H02M 1/53806; H01C 7/008; H01C 17/00; G01R 31/2642;
(Continued)

(56) References Cited

U.S. PATENT DOCUMENTS 3,504,544 A * 4/1970 Tymkewicz ........... G01K 1/146
374/163
3,662,259 A 5/1972 Dapilito
(Continued)

OTHER PUBLICATIONS

International Search Report and Written Opinion issued in PCT/US2016/032326 dated Sep. 9, 2016, 16 pages.

*Primary Examiner* — Manish S Shah
(74) *Attorney, Agent, or Firm* — Pearne & Gordon LLP (57) ABSTRACT

A meat probe has a shaft, plug, and stabilizer for measuring a parameter (e.g., temperature) of a piece of meat and communicating the measurement to a cooking appliance. The stabilizer may have a plurality of wings. For example, two wings may be cantilevered about a proximal end that is at the shaft. As the shaft is inserted into the piece of meat, the wings are bent outwardly about the proximal end. In another example, four wings are connected on opposite ends to a first and second base, and the shaft extends through the first and second bases. As the shaft is inserted into the piece of meat, the second base is pushed upward, decreasing the distance between the first and second base and bending the wings about a middle portion.

25 Claims, 9 Drawing Sheets

(51) Int. Cl.
*G01N 33/12* (2006.01)
*G01K 1/02* (2006.01)
*H05B 1/02* (2006.01)
*H05B 6/64* (2006.01)

(52) U.S. Cl.
CPC ......... *H05B 1/0263* (2013.01); *H05B 6/6452* (2013.01)

(58) Field of Classification Search
CPC ....... G01R 31/048; G01R 31/40; G01J 5/004; G01J 5/043; G01J 5/0821; A47J 43/287; F16B 2/02; F16B 1/00; F16B 47/00; F16B 2001/0035; F16M 13/02; F16M 13/022
See application file for complete search history.

(56) References Cited

U.S. PATENT DOCUMENTS

| | | | |
|---|---|---|---|
| 3,988,930 A * | 11/1976 | Fitzmayer | G01K 1/08 374/E1.011 |
| 3,991,615 A * | 11/1976 | Hornung | G01K 1/08 374/E1.011 |
| 4,853,625 A | 8/1989 | Fodali et al. | |
| 5,918,981 A * | 7/1999 | Ribi | G01K 1/16 374/162 |
| 5,983,783 A | 11/1999 | Archard et al. | |
| 6,000,845 A | 12/1999 | Tymkewicz et al. | |
| 6,065,391 A | 5/2000 | Archard et al. | |
| 7,880,487 B2 | 2/2011 | Petrick | |
| 8,154,316 B2 | 4/2012 | Lagerberg et al. | |
| 8,556,502 B2 | 10/2013 | Austen et al. | |
| 8,766,144 B2 | 7/2014 | McLoughlin et al. | |
| 2012/0119771 A1 | 5/2012 | Lagerberg et al. | |

* cited by examiner

ADJUSTABLE-LENGTH TEMPERATURE PROBE

BACKGROUND OF THE INVENTION

1. Field of the Invention

This application relates generally to a probe and, more specifically, to a temperature probe for food, and particularly for meat, that can be supported at various degrees and depths of insertion.

2. Description of Related Art

Temperature probes are often used in cooking during the preparation of foods. For example, the temperature or humidity/moisture level of meat can be used as an indicator of how well-done or well-cooked the food is. In many instances, it is desirable to place the probe in the thickest part of the meat or other food. However, the probe may need to be inserted at different depths and different angles depending on the type of food item, the size of the food item, the shape of the food item, and/or similar characteristics. For example, the probe may only need to be inserted a few centimeters in a turkey, while it may need to be inserted a few inches for a rib roast.

BRIEF SUMMARY OF THE INVENTION

According to one example described herein, a probe for sensing a parameter of an object comprises: a shaft having a distal end configured to be inserted into an object; and a stabilizer configured to contact the object upon insertion therein of said shaft and effective to stabilize the probe at a desired degree of insertion of said shaft in said object.

In various embodiments of the above example, the stabilizer comprises a plurality of wings cantilevered from or adjacent said shaft at a location remote from said distal end; each of said plurality of wings is configured such that said wings become increasingly more deflected outward from said shaft as said degree of insertion increases; the wings comprise textured inner surfaces in order to increase frictional contact between them and said object upon engagement against said object as said degree of insertion increases; the wings are biased toward a resting position that is substantially parallel with said shaft; the wings comprise lips at their respective distal ends; the wings are made of silicone; said probe is configured to measure a temperature of a food item while said meat is cooking, said shaft being insertable into said meat; said shaft is configured to transmit an electrical signal to a controller of cooking appliance representative of a temperature of the meat as it is cooking; said probe is configured to transmit a signal indicative of a temperature of a piece of meat while said meat is cooking, said shaft being partially insertable into said meat such that upon insertion thereof, said plurality of wings exert a clamping force against said meat that assists to secure said probe in place despite being only partially inserted; said stabilizer is further configured to increase an effective surface area of contact between said probe and said object across a range of insertion lengths of said shaft into said object; and/or said stabilizer adapts and conforms continuously as the shaft is inserted until a desired insertion length is reached.

According to another example described herein, a meat probe comprises: a shaft that is insertable into a piece of meat and that is effective to sense a parameter of the meat as the meat is cooked; a plug that communicates a signal representative of the parameter to a cooking appliance; and a stabilizer that stabilizes the shaft in a position such that the shaft remains at a desired position inside the meat.

In various embodiments of the above example, the stabilizer comprises a plurality of wings cantilevered from or adjacent said shaft at a location remote from an end configured to be inserted into the meat; the plurality of wings comprise textured surfaces that make contact with the meat as the shaft is inserted into the meat; the plurality of wings are made of silicone; the stabilizer comprises a plurality of wings attached on opposite ends to a first base and a second base and the shaft extends through middle portions of the first base and the second base; the shaft comprises at least one notch and the second base comprises at least one corresponding protrusion, such that the second base can be locked at a location along the shaft; the plurality of wings are formed of silicone encasing a piece of metal; as the shaft is inserted into the meat, the distance between the first base and the second base decreases and the wings are bent about a middle portion; the second base and/or the plurality of wings comprise textured surfaces that make contact with the meat as the shaft is inserted into the meat; the parameter is a temperature of the meat; the parameter is an electrical impedance of the meat; said stabilizer is further configured to increase an effective surface area of contact between said probe and said meat across a range of insertion lengths of said shaft into said meat; and/or said stabilizer adapts and conforms continuously as the shaft is inserted until a desired insertion length is reached.

DETAILED DESCRIPTION OF THE INVENTION

Certain terminology is used herein for convenience only and is not to be taken as a limitation on the claimed invention. Relative language used herein is best understood with reference to the drawings, in which like numerals are used to identify like or similar items. Further, in the drawings, certain features may be shown in somewhat schematic form.

While the following description is provided with respect to a temperature probe for food and more particularly for meat (and is therefore sometimes referred to below as a 'meat probe,' it is to be understood that the various aspects of the description may be used with other types of probes for other applications without diverting from the scope of the present disclosure. That is, the aspects described herein may be used for any probe that can be inserted at various angles and/or depths into an object in order to measure or sense parameters of that object, such as temperature or humidity. For example, aspects described herein can be equally applicable to humidity/moisture probes for cooking applications, as well as voltage and current probes in electrical applications.

Figure 1:
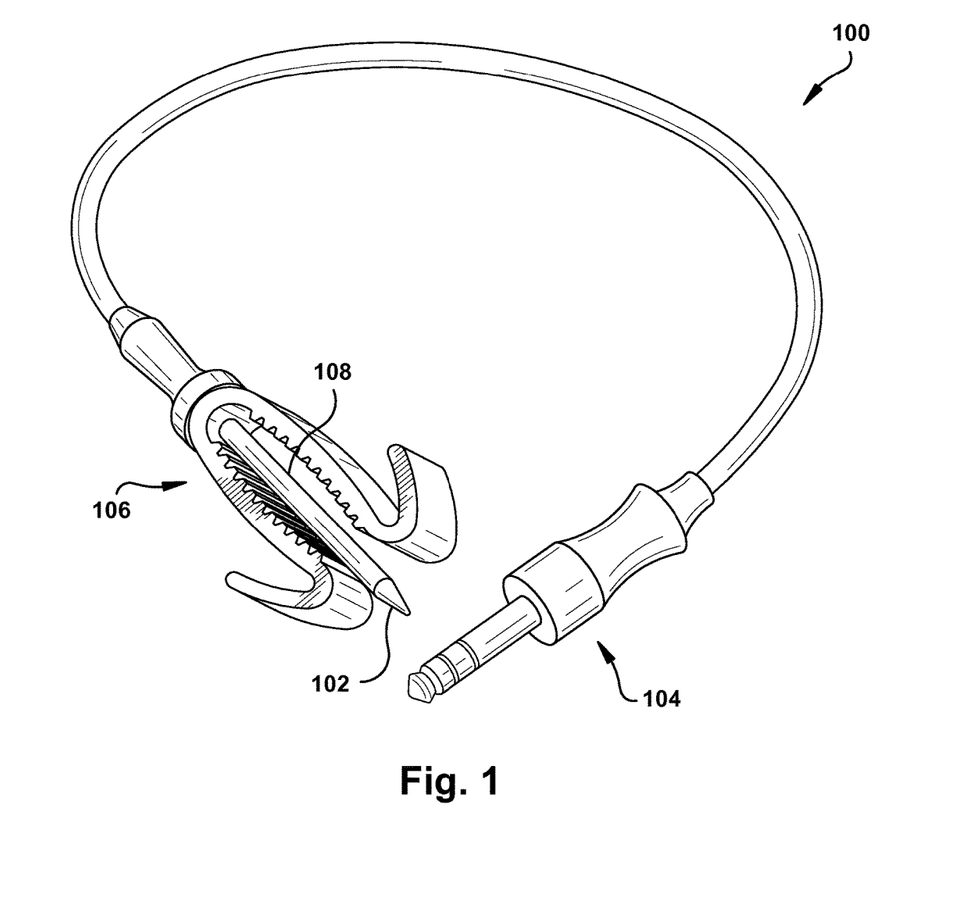
FIG. 1 is a perspective view of an example temperature probe.

FIG. 1 illustrates a perspective view of an example meat probe 100 capable of supporting a variable desired insertion length into a food item 802. Generally, the meat probe 100 can be understood to include a shaft 102, a plug 104, and a stabilizer 106. In the illustrated embodiment the shaft 102 is metal with a sharpened end for penetrating the meat or food to be monitored. The shaft 102 may include a thermocouple, thermistor, or the like, for measuring temperature, or may provide an electrically conductive path for determining a resistance/impedance used for measuring other properties of the meat as it is cooked. The plug 104 is electrically connected to the shaft 102, e.g. via a wire, so as to facilitate communication of an electrical signal indicative of or corresponding to measured parameter (e.g., temperature) to a processing or control device. In other embodiments, the plug 104 and the shaft 102 may be wirelessly connected.

Figure 9:
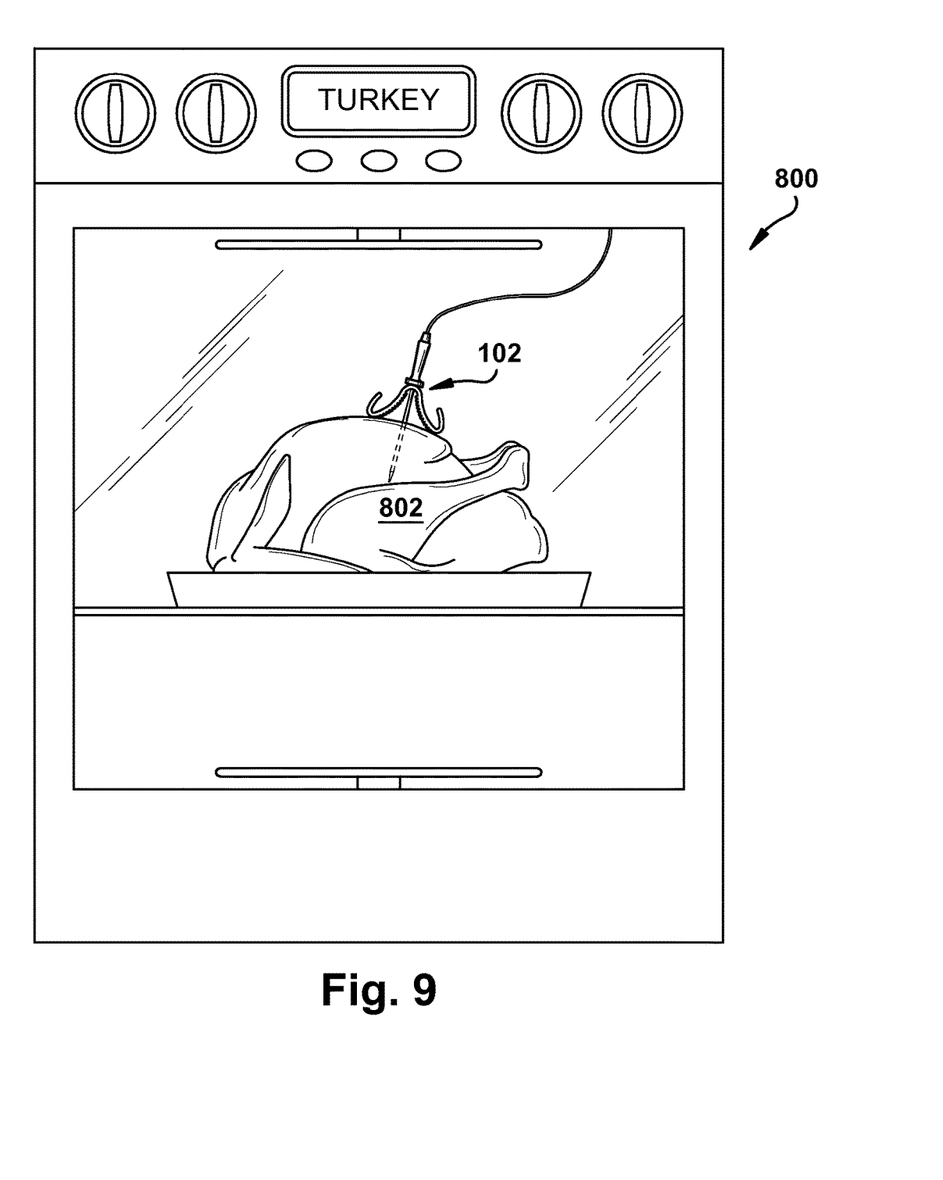
FIG. 9 illustrates an example temperature probe as used with a cooking appliance.

As illustrated in FIG. 9, the plug 104 of the meat probe 100 can be used to interface the shaft 102 with a cooking appliance (e.g., an oven) 800 in order to provide feedback relating to the appliance's cooking functions. It is also envisioned that the meat probe 100 can be utilized as a standalone device, in which the shaft 102 is connected to a smaller or handheld device with a processor and display for indicating measured parameters and controlling the function of the meat probe 100.

In embodiments involving an oven or other cooking appliance 800, the shaft 102 is inserted into a food item 802 (e.g. a turkey or rib roast) to monitor the internal temperature or other parameter (e.g. moisture) of the food item 802 as it cooks. The appliance 800 to which the meat probe 100 is connected has a controller (not shown), processor, or other electrical circuit, that monitors a parameter (e.g. temperature) within the food item 800 during the first part of a cooking cycle to generate a curve or function relating the parameter to cooking time. This curve or function may then be used to estimate the time remaining to completion of the cooking cycle (e.g., when the desired internal temperature will be reached) or to adjust the cooking cycle in accordance with a desired parameter, such as end cook time or temperature. For instance, once a temperature rise of approximately 100° has been achieved, there may be enough data to allow extrapolation of the curve or function to estimate the amount of time remaining until a target internal temperature of 160°, for example, will be reached.

Upon completion of cooking, an alarm can sound to alert a cook that a predetermined length of time (e.g., 15 min., 1 hour, etc.) remains in the cooking cycle to allow the cook to finalize the preparation of side dishes, set the table, and the like. Thus when the cooking cycle is complete, the food item 800 can be served with the side dishes while all food is hot. To ensure the actual completion time remains reasonably close to the estimated completion time as the cooking cycle progresses, the internal temperature of the food item may be continuously monitored even after the initial estimation, and the parameter, estimated completion time, and the like can be adjusted accordingly.

The stabilizer 106 stabilizes the meat probe 100 when the shaft 102 is inserted into the food item 802. To stabilize the meat probe 100, the stabilizer 106, for example, increases an effective surface area of between the meat probe 100 and a piece of meat across a range of insertion lengths of the shaft 102 into the meat. In other words, the stabilizer 106 may adapt and conform continuously as the shaft 102 is inserted until a desired insertion length is reached.

Figure 2:
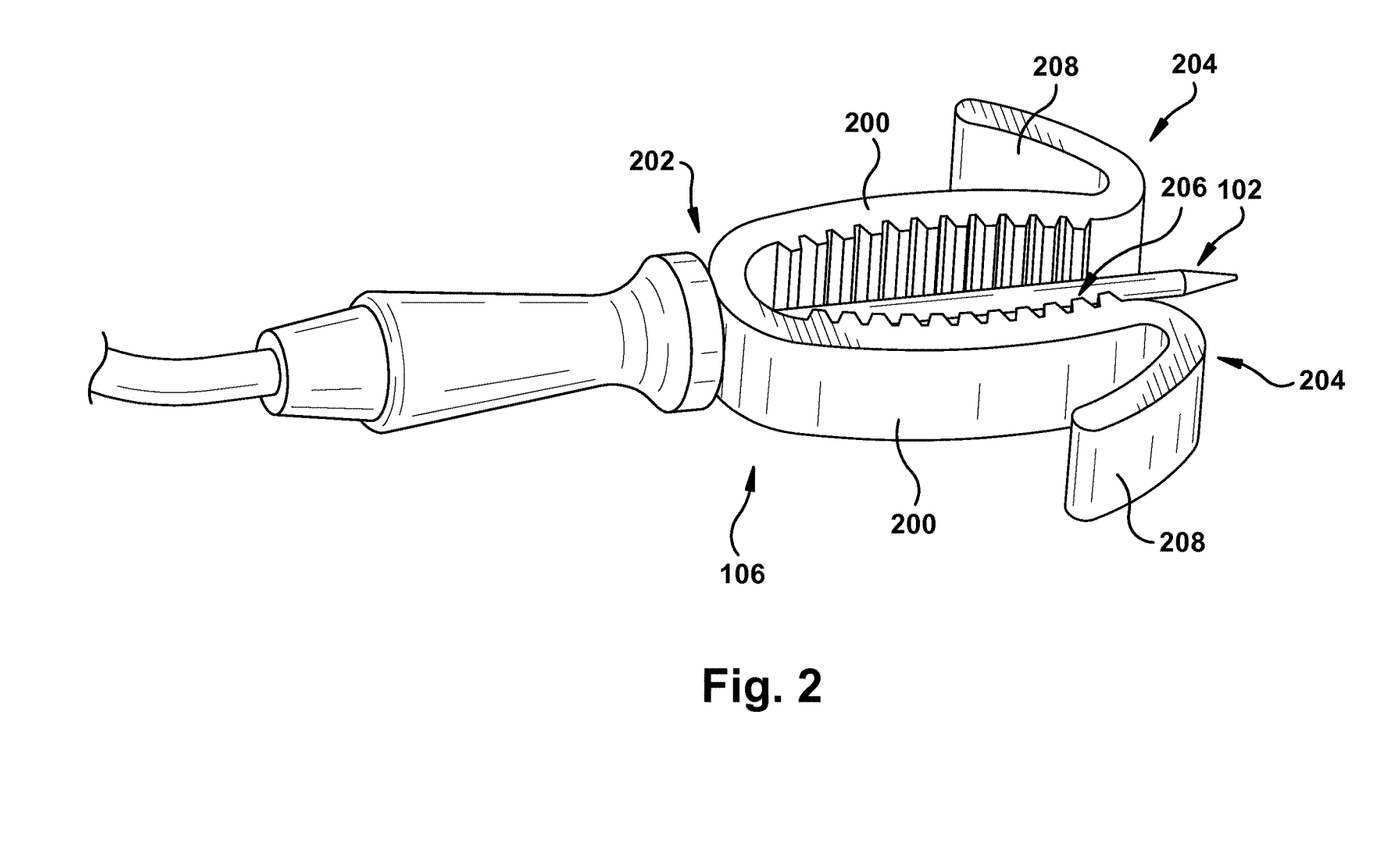
FIG. 2 is a further close-up perspective view of the probe of FIG. 1 showing a stabilizer of the probe in a resting position.
Figure 3:
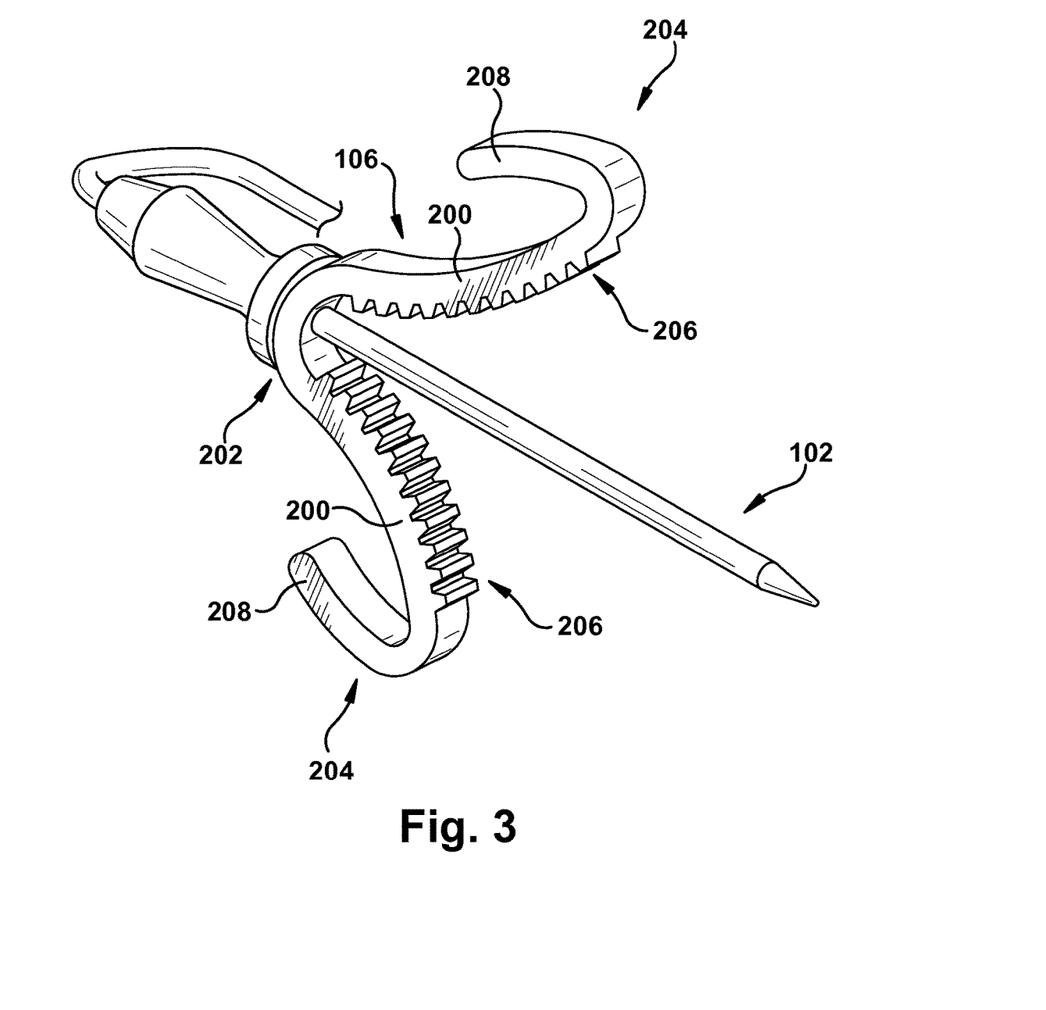
FIG. 3 is a perspective view as in FIG. 2 but showing the stabilizer in an example stressed or engaged position.

In the embodiment illustrated in FIGS. 1-3, the stabilizer 106 is formed of a plurality of wings 200 (two in the illustrated embodiment) cantilevered from adjacent the shaft at a location remote from the sharpened end. The plurality of wings 200 may be formed as a single unit or individually. In a resting position as shown in FIG. 2, the wings 200 are substantially parallel with the shaft 102. By 'substantially parallel' it is meant that the wings 200 extend generally along a common direction with the shaft 102 from the location 202 where they meet or are cantilevered adjacent the shaft 102. As seen, e.g. in FIG. 2, this does not necessarily mean that the wings 200 are truly parallel to the shaft 102, or even to each other along their full length. In a stressed or engaged position as shown in FIG. 3, the distal ends 204 of the respective wings 200 diverge outwardly, away from the shaft, for example in generally opposite directions, such that the distance from the shaft 102 to at least the distal end of at least one, and preferably of each, wing is increased. In the stressed position the distance between the distal ends 204 of at least one pair of adjacent wings is increased.

As can be seen in FIGS. 2 and 3, the wings 200 each have a textured inner surface 206, facing the shaft 102, for increasing resistance and friction between that surface of each of the wings 200 and the food item 802 as the shaft 102 is inserted into the food item 802. In the illustrated embodiment, the textured surfaces 206 are provided in the form of successive hills and valleys (e.g. grooves) extending transversely along the length of each wing 200, though other textures for increasing friction with contacted food items may be used. The distal ends 204 of the wings may also have a lip 208 for increasing structural mass at the distal ends 204, thereby increasing the supportive ability of the wings 200 and helping prevent rotation of the meat probe 100.

Figure 4:
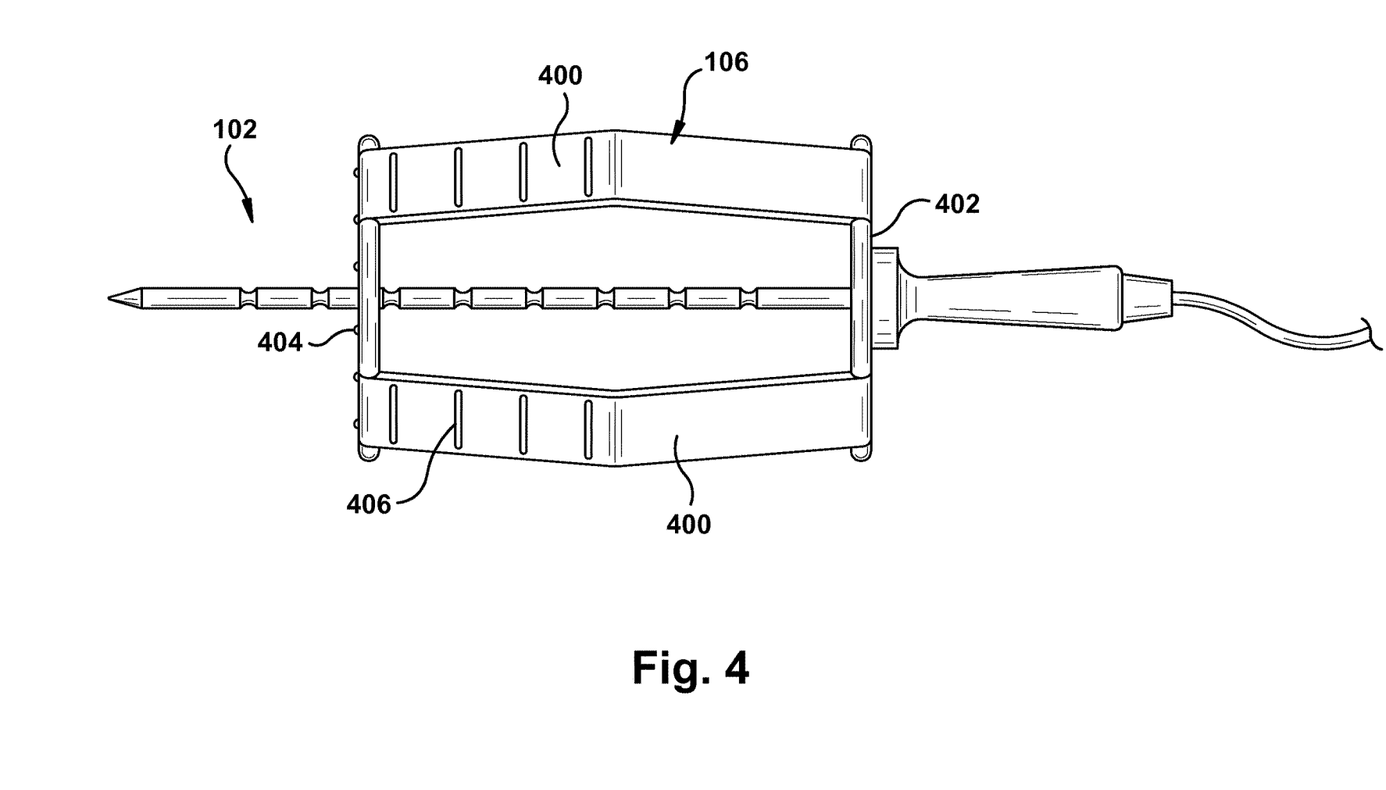
FIG. 4 is a perspective view of another example temperature probe having a stabilizer according to another embodiment in a resting position.
Figure 5:
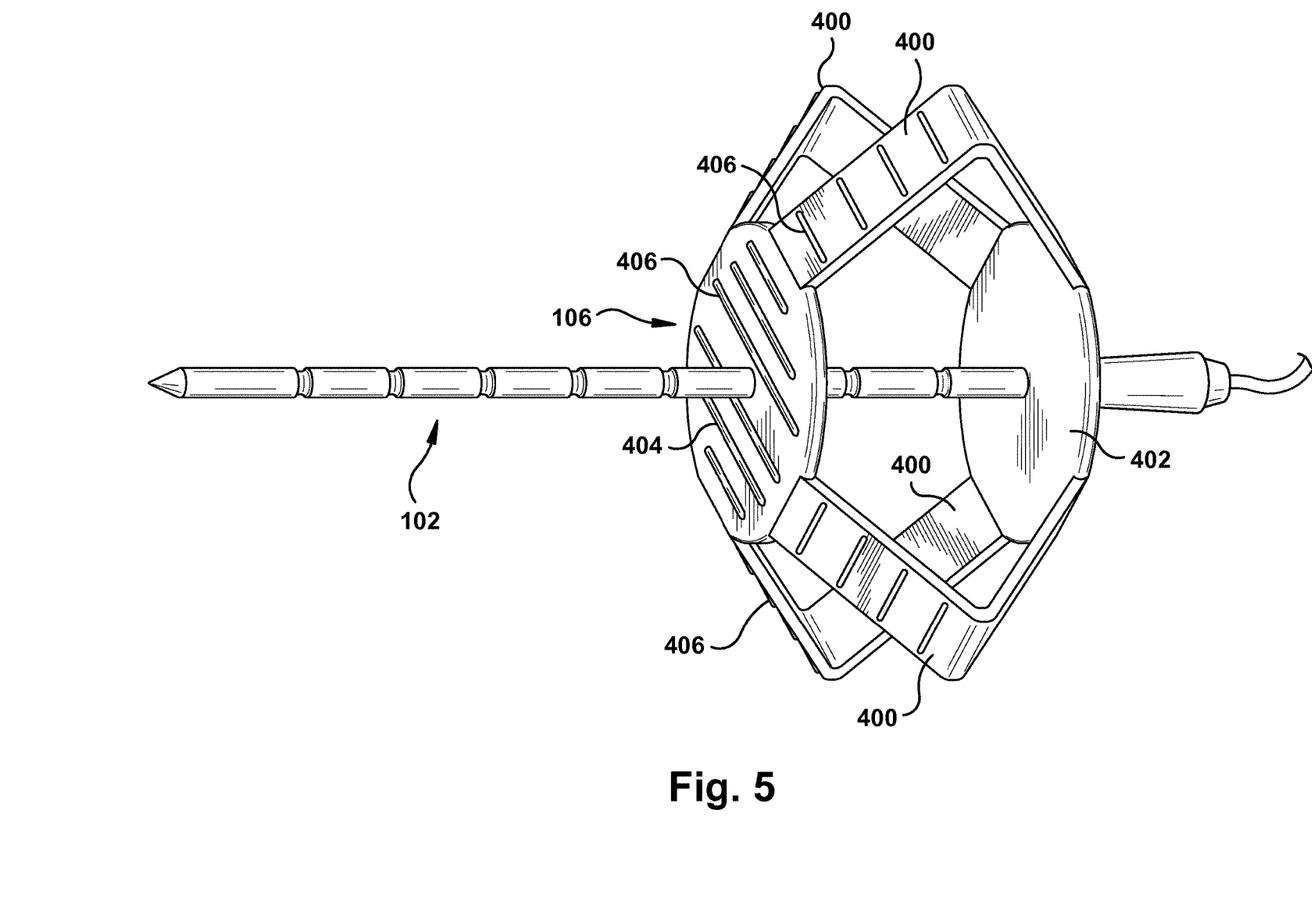
FIG. 5 is a perspective view of the probe of FIG. 4 but showing the stabilizer in an example stressed or engaged position.
Figure 6:
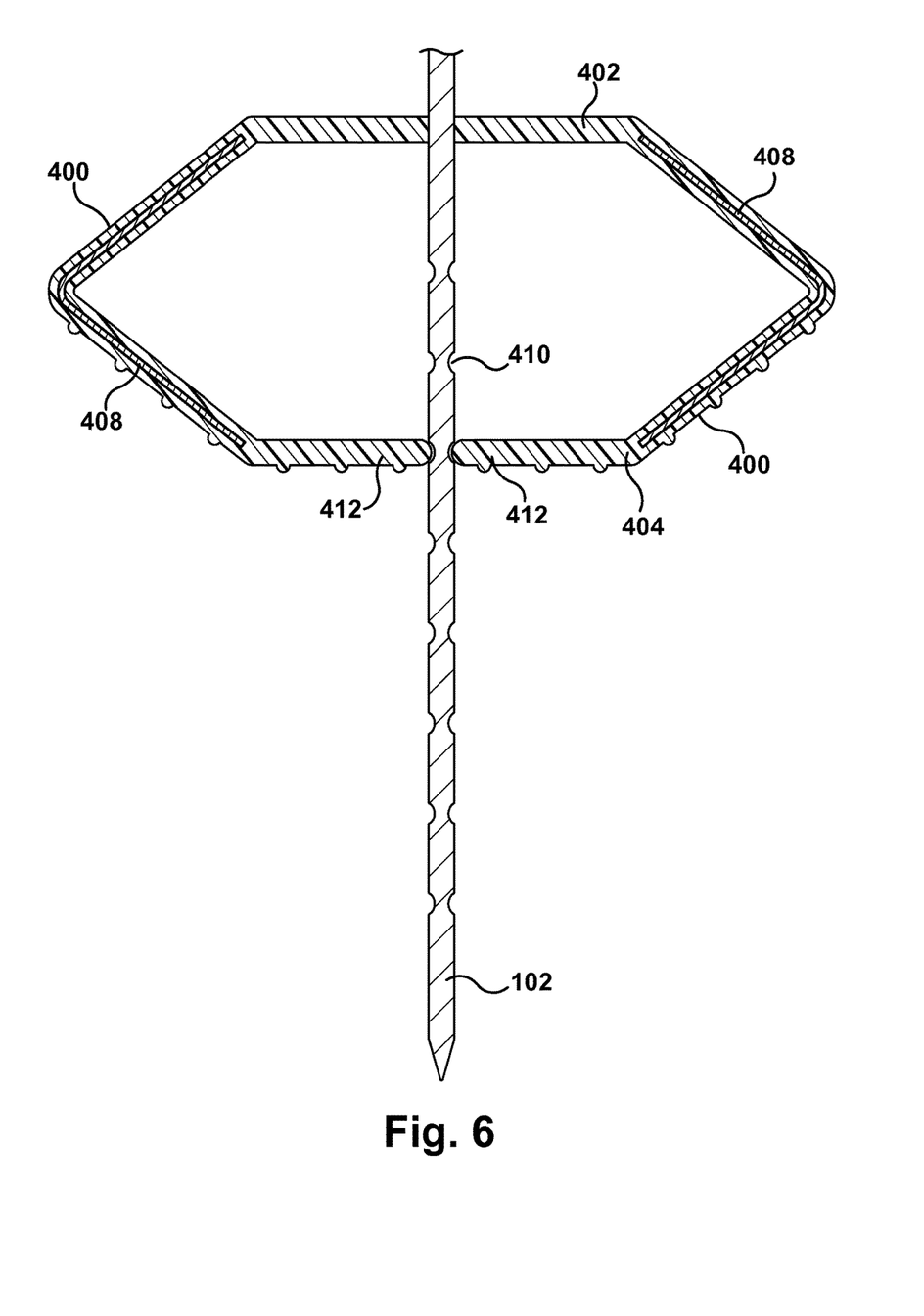
FIG. 6 is a cross section of the probe of FIG. 4, illustrating multiple embodiments for supporting the example stressed or engaged position of FIG. 5.
Figure 7A:
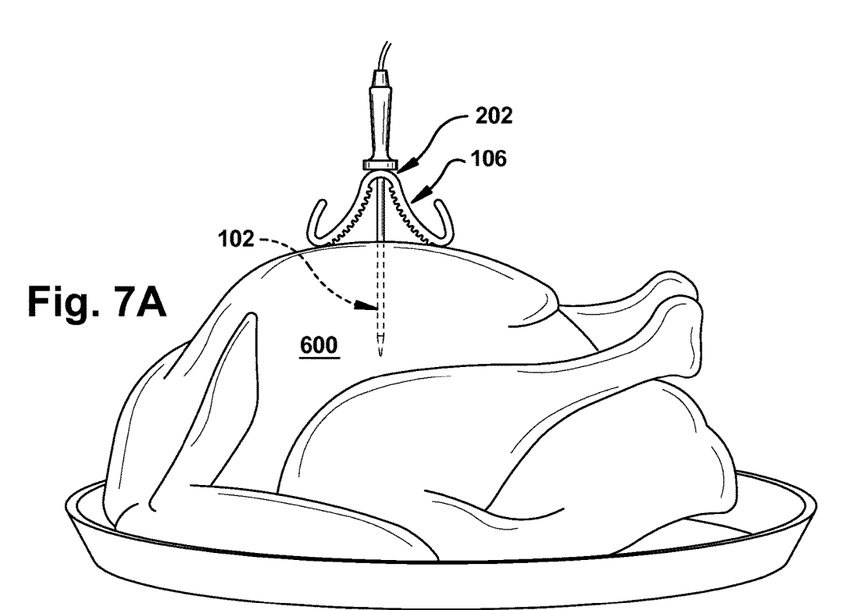
FIGS. 7A and 7B illustrate example temperature probes as used to measure a turkey.
Figure 7B:
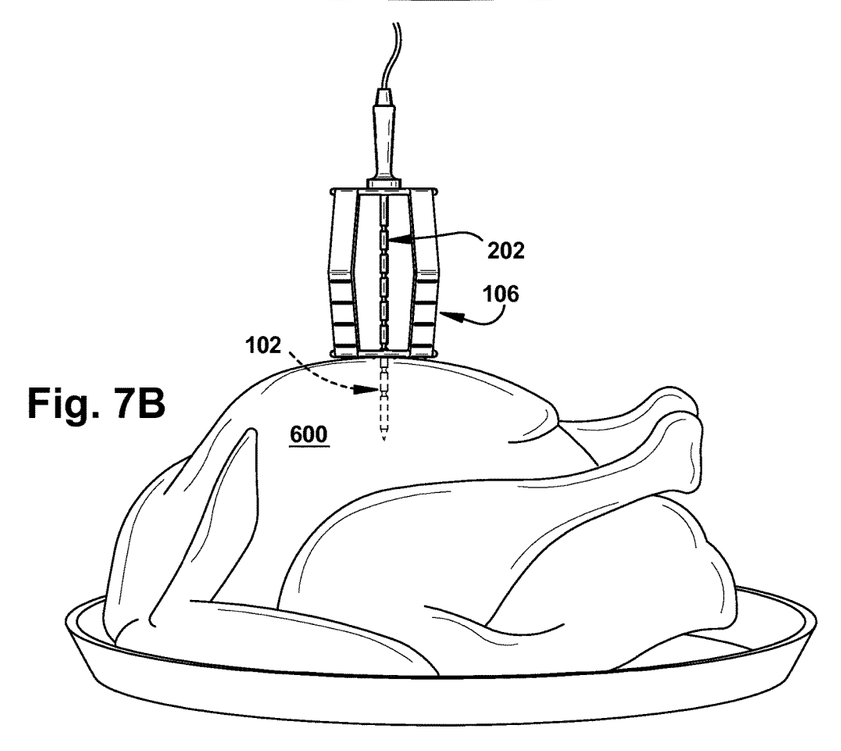
Figure 8A:
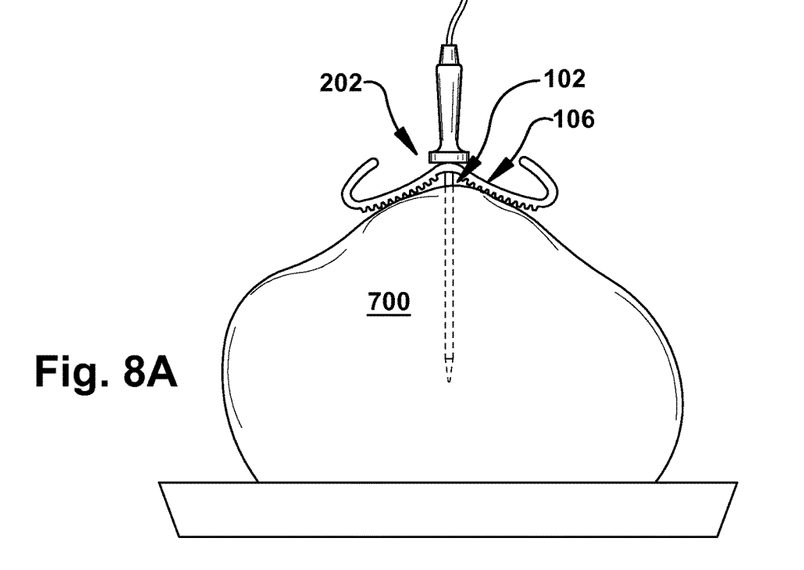
FIGS. 8A and 8B illustrate example temperature probes as used to measure a rib roast.
Figure 8B:
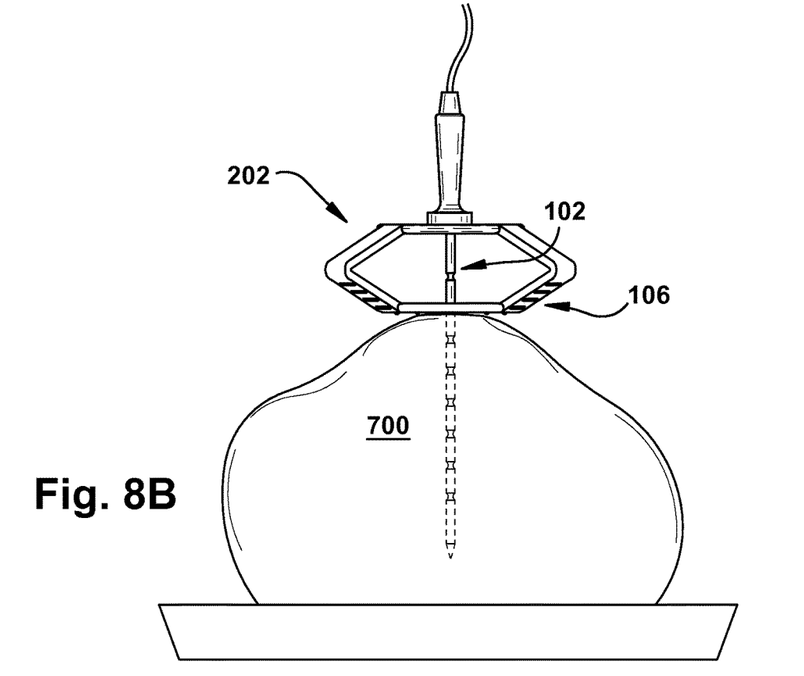

Another embodiment of a meat probe is illustrated in FIGS. 4-6. In this embodiment, the stabilizer 106 may also be formed as a plurality of wings 400 (e.g. four as shown in FIG. 4-6), with each wing 400 attached at its opposite ends to a first and second base 402, 404, respectively. As illustrated the first and second bases 402, 404 are circular, but they could take any shape. The shaft 102 is positioned through the middle of both the first and second bases 402, 404. The wings 400 are flexible such that first and/or second base 402, 404 may be moved axially along a length of the shaft 102 to vary the distance between the first and second bases 402, 404. Similar to the embodiments illustrated in FIGS. 1-3, the second base 404 and/or outer surfaces of the wings 400 may be textured, e.g. grooved, 406 as described above to provide increased friction with a food item.

To most effectively measure the desired parameter of the food item 802, the shaft 102 should be inserted into the food item 802 at a length depending on the size and type of the piece of the food item 802. For example, oftentimes it is desirable that the sharpened end of the shaft 102 rest near the center in the thickest part of the food item 802. FIGS. 7A and 7B, and 8A and 8B illustrate examples of how the meat probe may be used in a turkey 600 and rib roast 700, respectively. For the turkey 600 in FIGS. 7A and 7B the shaft 102 is inserted only a small amount, perhaps a few centimeters. In contrast, the shaft 102 is fully inserted into the rib roast 700 in FIGS. 8A and 8B.

To support and stabilize the shaft 102 whether it needs to be inserted only a centimeter or a few inches, the wings 200 of the embodiments illustrated in FIGS. 1-3 are flexible at least adjacent to their proximal ends 202 where they are cantilevered from or adjacent the shaft 102, so they can bend outward about their cantilevered ends as the shaft 102 is inserted. The wings 200 are biased toward a substantially parallel (as described above) resting position as illustrated in FIG. 2 such that when bent outward, the wings 200 cooperate to exert a clamping force on the food item 802 tending generally toward the shaft 102 located between the opposed wings 200. This clamping force helps support the shaft 102 in the food item 802 regardless of the degree or angle of insertion.

For the embodiment illustrated in FIGS. 4-6, the wings 400 may be biased toward a resting position (as illustrated in FIG. 4) where the first and second bases 402, 404 are at or near their greatest separation. Alternatively, in another example the wings 400 may have a piece or strip of ductile metal 408 embedded within or forming them to make them more posable in a range of discrete positions (poses'). That is, the metal 408 could be an alloy having high plastic deformation without or with a reduced tendency to snap or break as the metal is bent back-and-forth, such as aluminum or copper alloys. Thus, as the wings 400 are bent, the metal therein is bent to assume the new shape of the wing 400, and support the wing 400 in maintaining the bent shape. While the metal strips 408 (seen in FIG. 6) are illustrated as extending the length of the wing 400, the metal strips 408 may be smaller, for example extending only in the area of the wing 400 subject to bending. In other embodiments, the shaft 102 may comprise at least one notch 410, and the second base 404 may comprise at least one corresponding protrusion 412 (for example the edge of the opening in the base 404 through which the shaft 102 extends) such that the second base 404 may lock in at distinct locations along the axis of the shaft 102. Thus, again, as the wings 400 are bent, the second base 404 locks into a location to maintain and support the bent shape.

In this way, as the shaft 102 is inserted into the food item 802, the second base 404 is pressed upward by the food item 802, decreasing the distance between the first and second bases 402, 404 and bending the wings 400 are successively further outward. This effectively creates a wider base on which the meat probe 100 may rest against the food item 802 to increase support and prevent rotation and tipping of the meat probe. When the meat probe 100 is removed from the food item 802, the wings 404 may pressed together, or the second base 404 pulled downward, to return the meat probe 100 to the resting position.

The grooves 206, 406 of the wings 200, 400 may constitute a series of laterally-extending barbs or teeth, which grip the food item 802 as they are urged against the food item 802 with further insertion of the shaft 102 into the food item 802. As illustrated in FIGS. 7A and 7B, and 8A and 8B, the greater the degree of insertion, the greater may be the degree of contact between the grooves 206, 406, and the food item 802.

In order to withstand potentially high temperatures to which the meat probe 100 may be exposed inside of an oven or cooking appliance 800, the meat probe 100 may be made from combinations of materials with high melting points. For example, the exposed electrical portions (e.g., the shaft 102) may be made from a conductive metal such as steel; and the stabilizer 106 and cover for the wire attaching the shaft 102 to the plug 104 may be made from silicone.

What is claimed is:

1. A probe for sensing a parameter of an object, the probe comprising:
    a shaft having a distal end configured to be inserted into an object; and
    a stabilizer configured to:
        contact the object upon insertion therein of said shaft and effective to stabilize the probe at a desired degree of insertion of said shaft in said object, and
        increase an effective surface area of contact between said stabilizer and said object across a range of insertion lengths of said shaft into said object.

2. The probe according to claim 1, said probe being configured to measure a temperature of meat while said meat is cooking, said shaft being insertable into said meat.

3. The probe according to claim 2, said shaft being configured to transmit an electrical signal to a controller of a cooking appliance representative of a temperature of a food item as it is cooking.

4. The probe according to claim 1, wherein said stabilizer adapts and conforms continuously as the shaft is inserted until a desired insertion length is reached.

5. A probe, for sensing a parameter of an object, the probe comprising:
    a shaft having a distal end configured to be inserted into an object; and
    a stabilizer configured to contact the object upon insertion therein of said shaft and effective to stabilize the probe at a desired degree of insertion of said shaft in said object, the stabilizer comprising a plurality of wings cantilevered from or adjacent said shaft at a location remote from said distal end.

6. The probe of claim 5, each of said plurality of wings being configured such that said wings become increasingly more deflected outward from said shaft as said degree of insertion increases.

7. The probe according to claim 6, the wings being biased toward a resting position that is substantially parallel with said shaft.

8. The probe according to claim 5, the wings comprising textured inner surfaces in order to increase frictional contact between them and said object upon engagement against said object as said degree of insertion increases.

9. The probe according to claim 8, said probe being configured to transmit a signal indicative of a temperature of a piece of meat while said meat is cooking, said shaft being partially insertable into said meat such that upon insertion thereof, said plurality of wings exert a clamping force against said meat that assists to secure said probe in place despite being only partially inserted.

10. The probe according to claim 5, the wings comprising lips at their respective distal ends.

11. The probe according to claim 5, the wings being made of silicone.

12. The probe of claim 5, wherein the stabilizer is further configured to increase an effective surface area of contact between said stabilizer and said object across a range of insertion lengths of said shaft into said object.

13. The probe according to claim 12, wherein said stabilizer adapts and conforms continuously as the shaft is inserted until a desired insertion length is reached.

14. The probe according to claim 5, said probe being configured to measure a temperature of meat while said meat is cooking, said shaft being insertable into said meat.

15. The probe according to claim 5, said shaft being configured to transmit an electrical signal to a controller of a cooking appliance representative of a temperature of a food item as it is cooking.

16. A meat probe comprising:
 a shaft that is insertable into a piece of meat and that is effective to sense a parameter of the meat as the meat is cooked;
 a plug that communicates a signal representative of the parameter to a cooking appliance; and
 a stabilizer that stabilizes the shaft in a position such that the shaft remains at a desired position inside the meat, and that increases an effective surface area of contact between said stabilizer and said meat across a range of insertion lengths of said shaft into said meat.

17. The meat probe according to claim 16, wherein the parameter is a temperature of the meat.

18. The meat probe according to claim 16, wherein the parameter is an electrical impedance of the meat.

19. The meat probe according to claim 16, wherein said stabilizer adapts and conforms continuously as the shaft is inserted until a desired insertion length is reached.

20. A meat probe comprising:
 a shaft that is insertable into a piece of meat and that is effective to sense a parameter of the meat as the meat is cooked;
 a plug that communicates a signal representative of the parameter to a cooking appliance; and
 a stabilizer that stabilizes the shaft in a position such that the shaft remains at a desired position inside the meat,
 wherein the stabilizer comprises a plurality of wings cantilevered from or adjacent said shaft at a location remote from an end configured to be inserted into the meat.

21. The meat probe of claim 20, wherein the plurality of wings comprise textured surfaces that make contact with the meat as the shaft is inserted into the meat.

22. The meat probe of claim 21, wherein the plurality of wings are made of silicone.

23. The meat probe of claim 20, wherein the stabilizer further increases an effective surface area of contact between said stabilizer and said meat across a range of insertion lengths of said shaft into said meat.

24. The meat probe according to claim 20, wherein the parameter is a temperature of the meat.

25. The meat probe according to claim 20, wherein the parameter is an electrical impedance of the meat.

\* \* \* \* \*